(12) United States Patent         (10) Patent No.:     US 7,898,201 B2
Fisher et al.                     (45) Date of Patent:      Mar. 1, 2011

(54) RECEPTACLE FOR MEDICAL REFUSE

(76) Inventors: Cherie K. Fisher, North Smithfield, RI (US); Karen L. LeBoeuf, Lincoln, RI (US)

( * ) Notice: Subject to any disclaimer, the term of this patent is extended or adjusted under 35 U.S.C. 154(b) by 221 days.

(21) Appl. No.: 11/983,808

(22) Filed: Nov. 9, 2007

(65) Prior Publication Data

US 2008/0139866 A1    Jun. 12, 2008

Related U.S. Application Data

(60) Provisional application No. 60/858,264, filed on Nov. 9, 2006.

(51) Int. Cl.
*G05D 3/00* (2006.01)
(52) U.S. Cl. ........................ 318/466; 318/280
(58) Field of Classification Search ............... 318/466, 318/443, 468, 445, 280, 283
See application file for complete search history.

(56) References Cited

U.S. PATENT DOCUMENTS

| 4,576,281 | A | | 3/1986 | Kirksey | |
|---|---|---|---|---|---|
| 4,715,498 | A | * | 12/1987 | Hanifl | 206/366 |
| 4,890,733 | A | | 1/1990 | Anderson | |
| 5,076,429 | A | | 12/1991 | Patrick et al. | |
| 5,103,997 | A | | 4/1992 | Shillington et al. | |
| 5,185,126 | A | * | 2/1993 | Adamski et al. | 422/38 |
| 5,447,685 | A | * | 9/1995 | Sievert et al. | 422/22 |
| 5,639,031 | A | * | 6/1997 | Wright et al. | 241/33 |
| 5,740,909 | A | * | 4/1998 | Nazare et al. | 206/366 |
| 6,323,782 | B1 | | 11/2001 | Stephens et al. | |
| 6,759,959 | B2 | | 7/2004 | Wildman | |
| 6,957,767 | B2 | | 10/2005 | Aupperle et al. | |
| 6,998,541 | B2 | | 2/2006 | Morris et al. | |
| 7,114,629 | B2 | | 10/2006 | Panek, Jr. | |
| 7,119,689 | B2 | | 10/2006 | Mallett et al. | |
| 2002/0099334 | A1 | | 7/2002 | Hanson et al. | |
| 2002/0196150 | A1 | | 12/2002 | Wildman | |
| 2004/0008123 | A1 | | 1/2004 | Carrender et al. | |
| 2004/0129716 | A1 | * | 7/2004 | Naufel et al. | 221/9 |

* cited by examiner

*Primary Examiner*—Rina I Duda
(74) *Attorney, Agent, or Firm*—Kriegsman & Kriegsman

(57) ABSTRACT

A medical waste receptacle includes a housing shaped to define an interior cavity into which a waste collection bin is disposed. The housing is also shaped to include a slot in communication with the interior cavity, the slot being selectively enclosed by a disposal drawer adapted to pivot between closed and open positions. A movable latch selectively engages the drawer, the position of the latch being regulated by an electronic controller. In use, a barcode scanner in electrical connection with the controller retrieves an access code provided on a refuse container to be dispensed. If the access code is deemed valid, the controller disengages the latch from the drawer, thereby enabling the container to be dispensed into the bin through the slot. In the absence of receiving a valid access code, the controller retains the latch in engagement with the naturally closed disposal drawer, thereby precluding access to the bin.

12 Claims, 6 Drawing Sheets

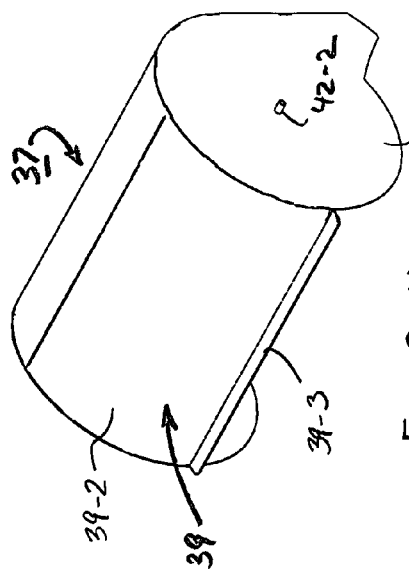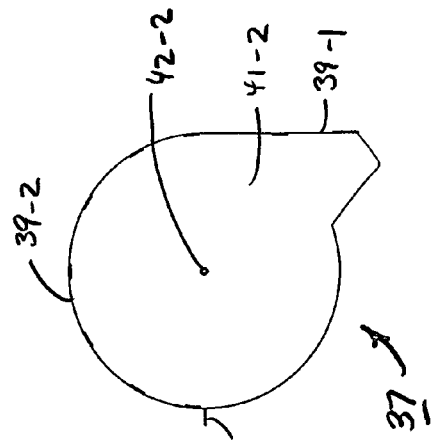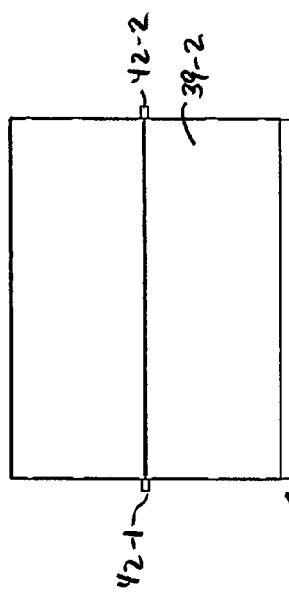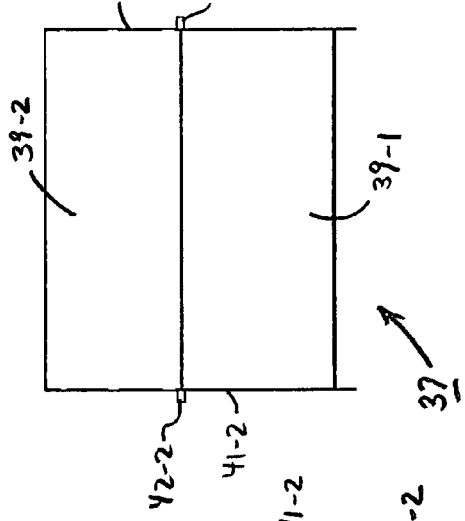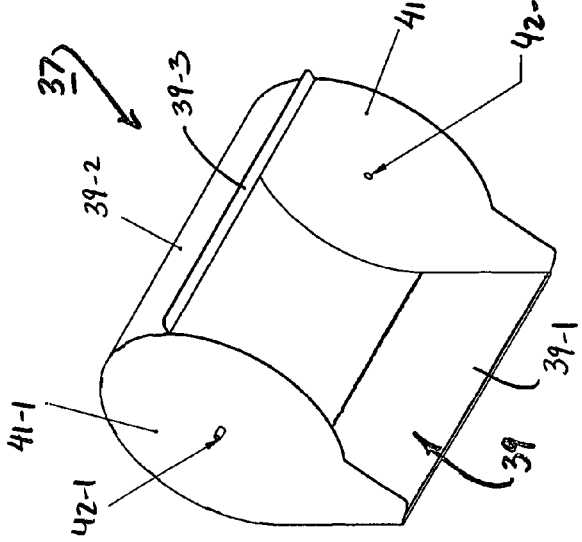

RECEPTACLE FOR MEDICAL REFUSE

CROSS-REFERENCE TO RELATED APPLICATIONS

The present application claims the benefit under 35 U.S.C. 119(e) of U.S. provisional Patent Application Ser. No. 60/858,264, filed Nov. 9, 2006, the disclosure of which is incorporated herein by reference.

BACKGROUND OF THE INVENTION

The present invention relates generally to the disposal of medical refuse and more particularly to receptacles used to safely collect medical refuse prior to professional disposal.

Medical treatments are commonly administered in a residential setting. As a result, there has been found to be an increased accumulation of medical refuse (e.g., used syringes, used lancets, etc.) in residential communities. It has been found that most consumers dispose of medical refuse in the same manner in which other forms of waste are discarded. Specifically, medical refuse is typically disposed of either (i) by flushing the refuse down a toilet or (ii) by mixing the refuse with other forms of household trash. As can be appreciated, the disposal of medical waste using either of the methods noted above fails to adequately safeguard against both intentional and unintentional contact by the general public and consequently poses a significant safety risk to the residential community.

Accordingly, it is well-known in the art for medical waste receptacles to be located at well-known locations in a particular community (e.g., a police station, fire station, pharmacy). In use, consumers are requested to enclose the medical refuse (e.g., used needles) within a protective container (e.g., sharps container or coffee can) and discard the container into the medical waste receptacle. In time, the various refuse containers that collect within the centralized medical waste receptacle are handled and disposed of by professional medical disposal personnel. In this manner, exposure to the potentially harmful medical refuse by the general public is minimized, which is highly desirable.

Presently, medical waste receptacles have a mailbox-type design. Specifically, each receptacle includes an exterior housing that is constructed of a rigid and durable material, such as metal. A removable hazardous waste collection bin is removably disposed within the housing and is accessed through a narrow slot that is enclosed by a pivoting drop door. In use, residents of the community are required to open the drop door and deposit medical waste containers through the narrow slot in the housing. In turn, each container drops within the interior of the collection bin. Periodically, a waste collection professional removes the collection bin from the exterior housing via a locked access door and replaces the removed collection bin with a new, empty bin.

Medical waste receptacles of the type described above have been found to suffer from a couple notable shortcomings.

As a first shortcoming, medical waste receptacles of the type described above include no means for monitoring and/or controlling the level of refuse containers which collect within the bin. As a result, it has been found that receptacles of the type described above are commonly overfilled, thereby creating a potentially hazardous condition, which is highly undesirable.

As a second shortcoming, medical waste receptacles of the type described above include no means for restricting access to the collected refuse through drop door. As a result, it has been found that certain individuals attempt to retrieve medical refuse contained within the receptacle by sticking his/her hand through the narrow drop slot. As can be appreciated, the ability of these individuals to potentially access harmful refuse poses a significant safety risk to most communities, which is highly undesirable.

SUMMARY OF THE INVENTION

It is an object of the present invention to provide a novel receptacle for medical refuse.

It is another object of the present invention to provide a receptacle as described above which safely stores medical refuse collected therein.

It is yet another object of the present invention to provide a receptacle as described above which includes means for regulating the deposition of medical refuse therein.

It is still another object of the present invention to provide a receptacle as described above which monitors the level of refuse collected therein.

It is yet still another object of the present invention to provide a receptacle as described above which limits access to the medical refuse stored therein to authorized individuals.

It is yet another object of the present invention to provide a receptacle as described above which has a limited number of parts, is inexpensive to manufacture and is easy to use.

Accordingly, there is provided a receptacle for medical refuse, the receptacle comprising (a) a housing comprising a plurality of panels which together define an interior cavity, the housing being shaped to define a refuse deposition slot which is in communication with the interior cavity, (b) a drawer coupled to the housing and pivotable between closed and open positions, the drawer fully enclosing the slot when disposed in its closed position, the drawer at most partially enclosing the slot when disposed in its open position, (c) a latch disposable between first and second positions, the drawer being retained in its closed position by the latch when disposed in its first position, the drawer being capable of pivotable displacement between its closed and open positions when the latch is disposed in its second position, and (d) a electronic controller for regulating the position of the latch.

Various other features and advantages will appear from the description to follow. In the description, reference is made to the accompanying drawings which form a part thereof, and in which is shown by way of illustration, an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIGS. 3(a)-(e) are bottom perspective, top plan, rear plan, front perspective and right end views, respectively, of the disposal drawer shown in FIG. 1.

DETAILED DESCRIPTION OF THE PREFERRED EMBODIMENT

Construction of Waste Receptacle 11

Figure 1:
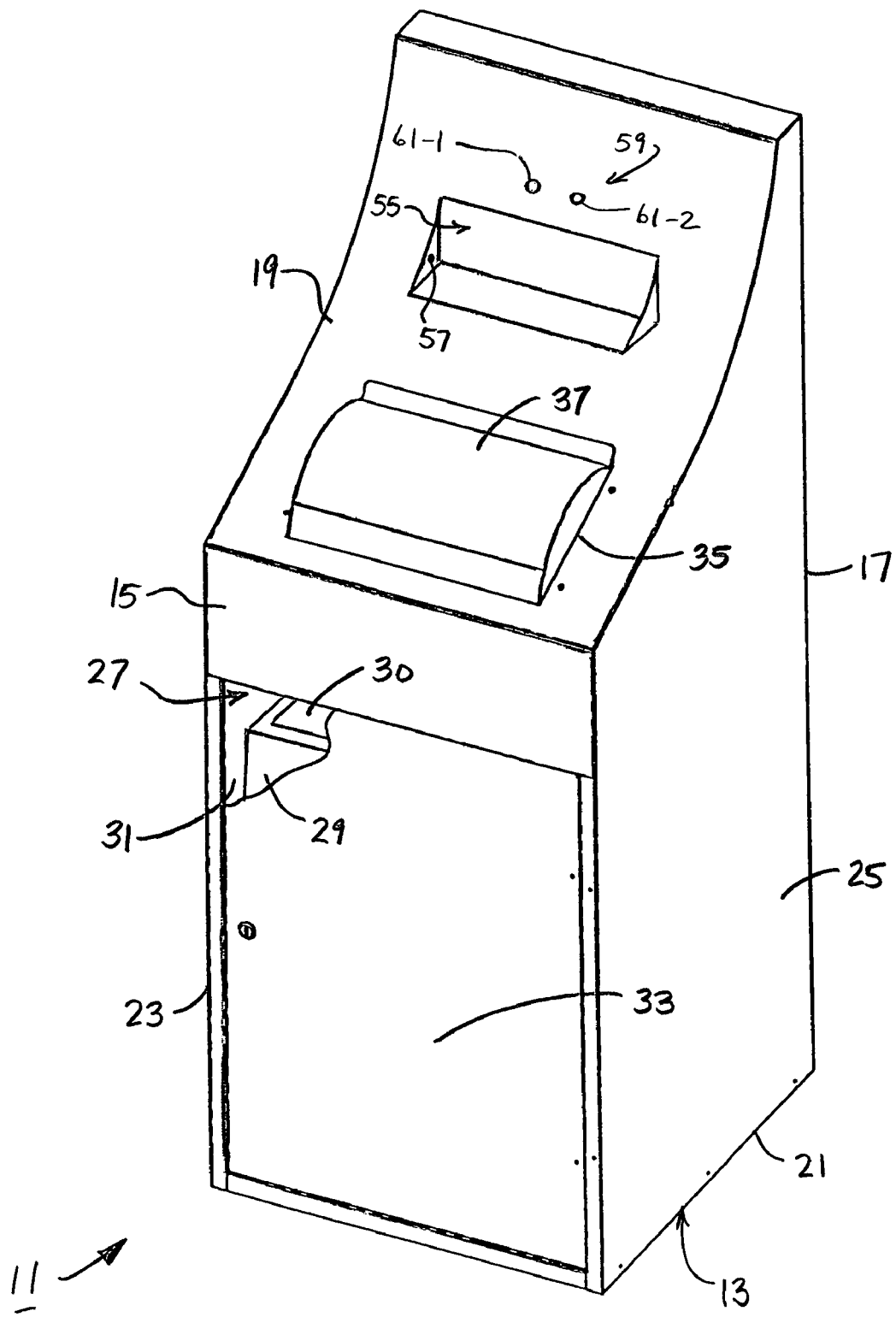
FIG. 1 is a front perspective view, broken away in part, of a medical waste receptacle constructed according to the teachings of the present invention, the medical waste receptacle being shown with a collection bin positioned therewithin.

Referring now to FIG. 1, there is shown a perspective view, broken away in part, of a medical waste receptacle constructed according to the teachings of the present invention and identified generally by reference numeral 11. As will be described in detail below, waste receptacle 11 precludes a user from depositing medical refuse therein unless, among other things, (i) the amount of refuse in waste receptacle 11 remains below a predetermined level and (ii) an approved access code is first received by waste receptacle 11.

Receptacle 11 comprises an exterior housing 13 that is constructed out of a rigid and durable material, such as fourteen gauge steel. As can be seen, housing 13 comprises a front panel 15, a rear panel 17, a top panel 19, a bottom panel 21, a left side panel 23 and a right side panel 25 which together define an interior cavity 27. Although not shown herein, it is to be understood that housing 13 could additionally include floor anchoring means without departing from the spirit of the present invention.

Housing 13 is sized and shaped to receive a removable hazardous waste collection bin 29 within its interior cavity 27. Waste collection bin 29 is represented herein as a five-sided box which is shaped to define an open top end 30, bin 29 being preferably constructed of a rigid and durable material, such as plastic.

Front panel 15 of housing 13 is provided with an enlarged opening 31 through which waste collection bin 29 can be externally accessed. Enlarged opening 31 is selectively enclosed by a lockable access panel 33 which is pivotally connected along one of its side edges to front panel 15 by a hinge (not shown). As can be appreciated, lockable access panel 33 restricts access to collection bin 29 to authorized waste disposal professionals.

Top panel 19 is shaped to include a refuse deposition slot, or passageway, 35 through which waste containers can be passed. Preferably, slot 35 is positioned directly above open top end 30 of collection bin 29. In this manner, containers passed through slot 35 drop directly inside collection bin 29.

Figure 2B:
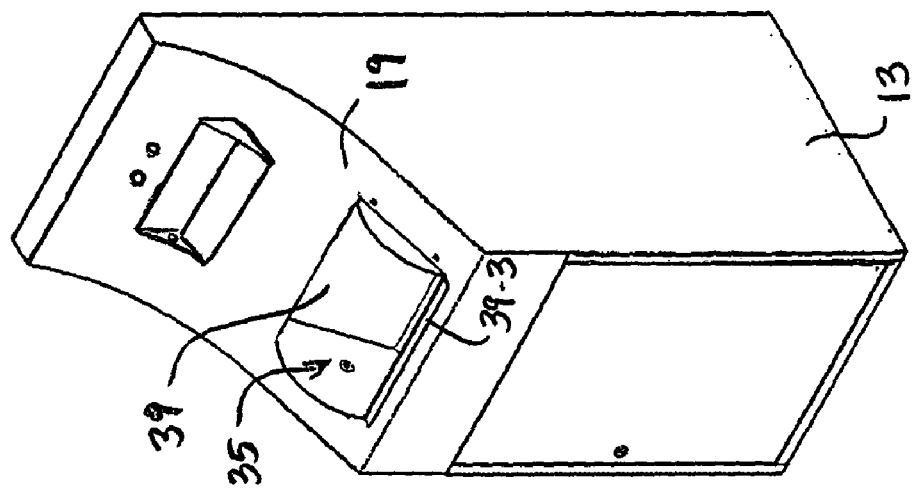
FIG. 2(b) is a front perspective view of the medical waste receptacle shown in FIG. 1, the medical waste receptacle being shown with its disposal drawer disposed in its open position.
Figure 2A:
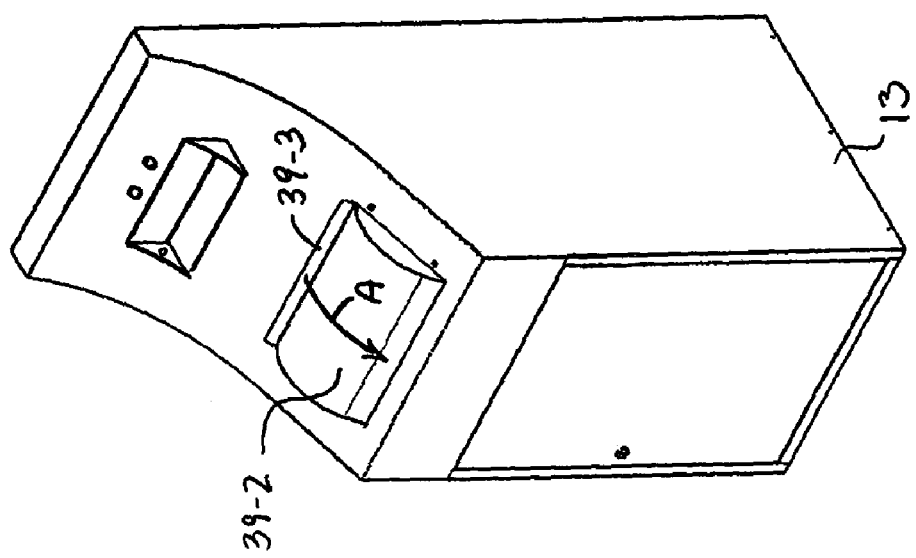
FIG. 2(*a*) is a front perspective view of the medical waste receptacle shown in FIG. 1, the medical waste receptacle being shown with its disposal drawer disposed in its closed position.

A disposal drawer 37 is coupled to top panel 19 and is capable of being pivotally displaced between a closed position, as shown in FIG. 2(a), and an open position, as shown in FIG. 2(b). In this manner, the displacement of drawer 37 serves to selectively enclose slot 35. It is to be understood that, with drawer 37 disposed in its closed position, interior cavity 27 of housing 13 is rendered externally inaccessible through slot 35.

Disposal drawer 37 is represented herein as being in the form of a roll bucket which is constructed of a rigid and durable sheet metal material. However, it is to be understood that disposal drawer 37 is not limited to a roll bucket design. Rather, disposal drawer 37 could be replaced with alternative types of access doors (e.g., a substantially planar drop door) without departing from the spirit of the present invention.

Referring now to FIGS. 3(a)-(e), disposal drawer 37 comprises a one-piece central tray 39 which includes a substantially planar section 39-1, an arcuate section 39-2 and an outwardly protruding flange 39-3 formed on the free end of arcuate section 39-2. Disposal drawer 37 additionally includes a pair of end pieces 41-1 and 41-2, each end piece 41 being in the form of a thin, generally circular plate. End pieces 41 are formed onto opposing side edges of central tray 39 so as to render disposal drawer 37 a unitary member. A pair of shortened cylindrical posts 42-1 and 42-2 extends orthogonally out from the approximate center of end pieces 41-1 and 41-2, respectively. As can be appreciated, posts 42 serve as pivot points about which drawer 37 can rotate relative to housing 13, with flange 39-3 serving as a handle for pivoting drawer 37.

As noted briefly above, disposal drawer 37 can be pivoted between a closed position and an open position. With bucket 37 disposed in its closed position, as shown in FIG. 2(a), the outer surface of arcuate section 39-2 fully encloses refuse deposition slot 35 and thereby effectively precludes medical refuse from being deposited into receptacle 11. It should be noted that disposal drawer 37 is preferably biased to its closed position for safety purposes. For example, a spring (not shown) which is connected at one end to housing 13 and at the other end to disposal drawer 37 may serve to resiliently bias disposal drawer 37 closed in a gradual manner (i.e., without forcefully slamming disposal drawer 37 shut).

Using flange 39-3 as a handle, disposal drawer 37 can be rotated forward (as represented by arrow A in FIG. 2(a)) to its open position, as shown in FIG. 2(b). With roll bucket 37 disposed in its open position, the inner surface of central tray 39 is rendered accessible through open slot 35 in top panel 19. In this manner, a waste container can be passed through slot 35 and positioned directly upon central tray 39. With a waste container placed on central tray 39, rotation of disposal drawer 37 back to its closed position causes the waste container to slide along tray 39 and drop through open top end 30 of waste collection bin 29.

As a principal feature of the present invention, receptacle 11 is provided with electronic means for selectively locking disposal drawer 37 in its closed position. Specifically, referring now to FIG. 4, an electronic controller 45 is provided within interior cavity 27 and is responsible for regulating the primary operations of receptacle 11. Although not shown herein, controller 45 is preferably powered by four C-cell alkaline batteries or any other similar power source.

Controller 45 comprises a printed circuit board (PCB) 47 which is fixedly mounted onto the inner surface of rear panel 17 and is preferably accessible though an access door (not shown) provided in panel 17. Controller 45 additionally includes a programmable microprocessor 49 which is mounted on printed circuit board 47. For example, microprocessor 49 may be in the form of a PIC16F916 model microchip of the type which is manufactured and sold by Microchip Technology, Inc. As can be appreciated, microprocessor 49 is programmed to regulate the principal operations of receptacle 11.

Waste receptacle 11 comprises a latch 51 which is configured to selectively engage disposal drawer 37. Specifically, latch 51 is capable of being displaced between a first (i.e., locked) position and a second (i.e., unlocked) position. With disposal drawer 37 disposed in its closed position, the displacement of latch 51 into its first position causes latch 51 to engage drawer 37 in such a manner so as to lockably retain disposal drawer closed (i.e., render drawer 37 incapable of pivotal displacement). Furthermore, the displacement of latch 51 into its second position causes latch 51 to disengage from drawer 37, thereby enabling disposal drawer 37 to freely rotate between its closed and opened positions.

Latch 51 is represented herein as being in the form of an elongated plate which is designed to selectively engage disposal drawer 37 (e.g., project through a slot formed in either drawer 37 or a bracket coupled to drawer 37). However, it should be noted that latch 51 is not limited to an elongated plate design. Rather, latch 51 could be alternatively configured (e.g., as a generally L-shaped or J-shaped hook that selectively protrudes through a corresponding slot in disposal drawer 37) without departing from the spirit of the present invention.

Latch 51 is preferably driven between its locked and unlocked positions by a solenoid 53 that is electrically connected to printed circuit board 47. Specifically, solenoid 53 is located within interior cavity 29 and includes a movable piston 53-1 on which latch 51 is mounted. As will be described further below, with solenoid 53 in its de-energized state, piston 53 extends outward in such a manner such that latch 51 engages disposal drawer 37. To the contrary, with solenoid in its energized state, piston 53 retracts such that latch 51 disengages from disposal drawer 37.

It is should be noted that the present invention is not limited to the use of solenoid 53 to drive latch 51 between its locked and unlocked positions. Rather, it is to be understood that latch 51 could be driven between its locked and unlocked positions by alternative means (e.g., a motor configured to rotate a hook-shaped latch into selective engagement with disposal drawer 37) without departing from the spirit of the present invention.

Figure 4:
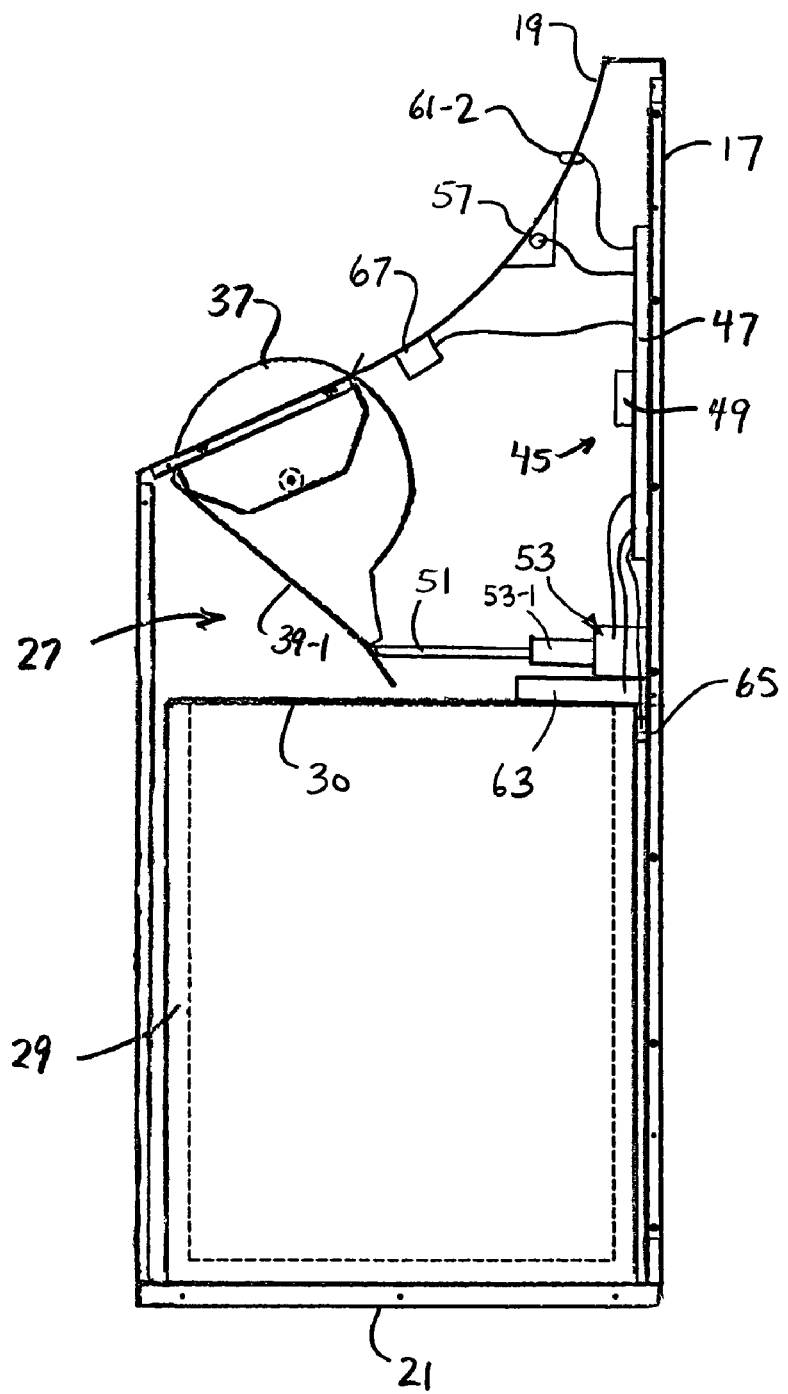
FIG. 4 is a right end view of the medical waste receptacle shown in FIG. 1, the medical waste receptacle being shown with its right side panel removed therefrom, the medical waste receptacle also being shown with a collection bin positioned therewithin.

Referring now to FIGS. 1 and 4, an elongated recess 55 is formed in top panel 19, recess 55 being represented herein as generally triangular lateral cross-section. A barcode reader, or scanner, 57 is preferably mounted on the inner surface of top panel 19 and is electrically connected to printed circuit board 47. Barcode reader 57 is mounted within interior cavity 27 such its optical scan line passes through a window, or opening, in top panel 19 and projects into recess 55. In this manner, reader 57 is designed to retrieve the identification code which relates to a barcode that is properly positioned within recess 55 and, in turn, pass the retrieved identification code to controller 45 for analysis. As will be described further in detail below, the deposition of refuse into receptacle 11 is only permitted if, among other things, controller 45 receives an authorized access code from reader 57.

It should be noted that receptacle 11 is not limited to the use of barcode reader 57 to retrieve an authorized access code. Rather, it is to be understood that alternative means for retrieving an access code which authorizes the deposition of medical refuse into receptacle 11 could be utilized without departing from the spirit of the present invention. As an example, it is to be understood that barcode reader 57 could be replaced with other forms of automatic identification means (e.g., a radio frequency identification (RFID) reader) without departing from the spirit of the present invention. As another example, it is to be understood that barcode reader 57 could be replaced with means for manually inputting an access code (e.g., an externally accessible keypad) without departing from the spirit of the present invention.

An externally viewable display 59 is provided in top panel 19, display 59 being in electrical connection with printed circuit board 47. Display 59 is represented herein as comprising a pair of individually operating indicator lights 61-1 and 61-2, light 61-1 being in the form of a red light emitting diode (LED) and light 61-2 being in the form of a yellow light emitting diode (LED). As will be described further in detail below, controller 45 is programmed to illuminate indicator lights 61 in a particular sequence when certain problematic conditions relating to the general operation of receptacle 11 are detected (e.g., a low power level, the absence of collection bin 29, a substantially full collection bin 29, etc.).

As can be appreciated, display 59 is not limited to a plurality of individually operable indicator lights 61. Rather, it is to be understood that display 59 could utilize alternative means of displaying information, such as a liquid crystal display (LCD) touch screen, without departing from the spirit of the present invention.

A sonar sensor 63 is mounted on rear panel 17 of housing 13 within interior cavity 27 and is in electrical connection with printed circuit board 47. Sonar sensor 63 is preferably disposed directly above open top end 30 of collection bin 29. In this manner, sonar sensor 63 can be used to routinely measure the level of waste collecting within bin 29. In turn, the waste level measurements recorded by sensor 63 are preferably monitored by controller 45 to prevent overfilling of collection bin 29, as will be described further below.

It should be noted that receptacle 11 is not limited to the use of sonar to measure the level of waste collecting within bin 29. Rather, it is to be understood that alternative waste level measurement means (e.g., acoustic resonance, optics, weight, etc.) could be utilized in place of sonar sensor 63 without departing from the spirit of the present invention.

As seen most clearly in FIG. 4, a bin detection sensor 65 is mounted on the inner surface of rear panel 17 in close proximity to collection bin 29, bin detection sensor 65 being in electrical connection with printed circuit board 47. As will be described further below, sensor 65 is provided to detect the presence of collection bin 29 within interior cavity 27. In addition, a drawer position sensor 67 is mounted on the inner surface of top panel 19 in close proximity to disposal drawer 37, drawer position sensor 67 being in electrical connection with printed circuit board 47. As will be described further below, sensor 67 sends a signal to controller 45 when drawer 37 is disposed in its closed position.

Operation of Waste Receptacle 11

Figure 5B:
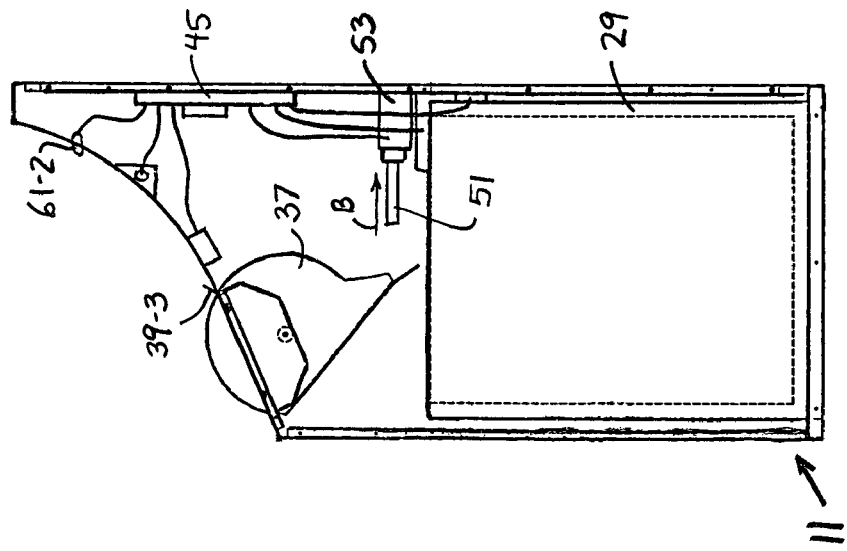
FIGS. 5(a)-(d) are right end views of the medical waste receptacle shown in FIG. 4 at various stages during the process of depositing a medical refuse container therein.
Figure 5A:
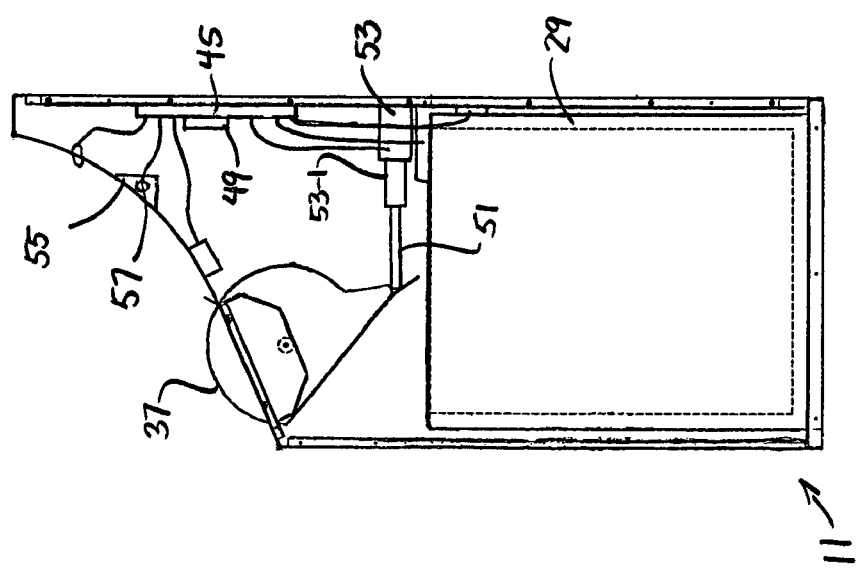
Figure 5D:
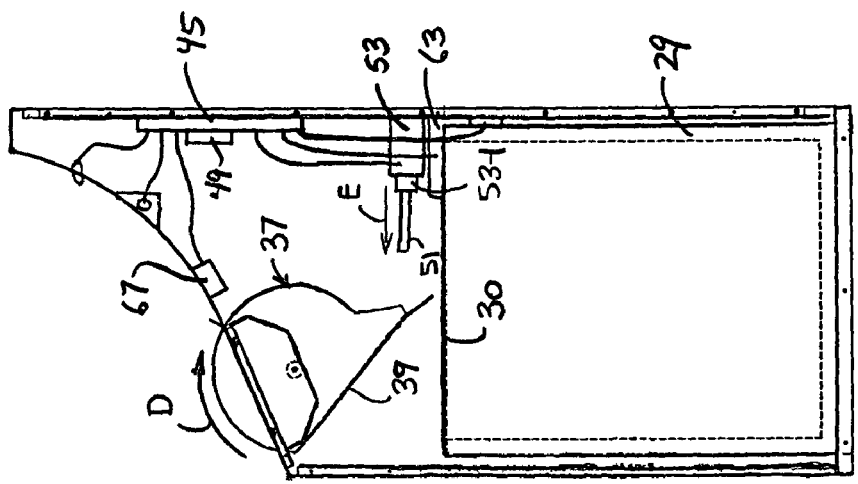
Figure 5C:
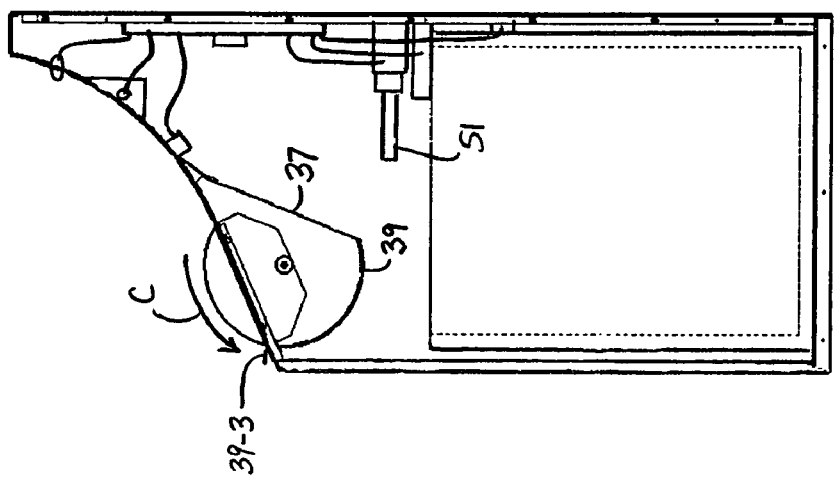

In use, waste receptacle 11 is designed to collect medical refuse in the following manner. Referring now to FIG. 5(a), prior to the deposition of any medical refuse into receptacle 11, it is to be understood that (i) disposal drawer 37 is resiliently biased into its closed position and (ii) solenoid 53 remains in its de-energized state. Accordingly, with solenoid 53 de-energized, piston 53-1 disposes latch 51 into its locked position, thereby effectively locking disposal drawer 37 in its closed position.

In order to deposit medical refuse (e.g., used syringes, used lancets, expired prescriptions, etc.) into waste receptacle 11, the medical refuse is first preferably deposited into a safety container (e.g., a sharps container) that is provided with a specified barcode on its exterior surface. When the user is ready to discard the safety container into waste receptacle 11, the user is required to place the container within recess 55. With the container positioned as such, barcode reader 57 retrieves the identification code provided in the container barcode and, in turn, sends the identification code to controller 45.

The identification code retrieved from the safety container functions as an access code which is cross-referenced by microprocessor 49 against a list of acceptable codes which are stored in memory for controller 45. If the retrieved access code is verified by microprocessor 49 as being valid (i.e., the access code matches an acceptable access code stored in memory), controller 45 in turn energizes solenoid 53. Once energized, solenoid 53 displaces latch 51 from its locked position to its unlocked position, as represented by arrow B in FIG. 5(*b*).

It should be noted that until controller 45 retrieves an acceptable access code, disposal drawer 37 remains locked in its closed position, thereby precluding an unauthorized person from accessing the medical refuse in collection bin 29 through slot 35. It is to be understood that controller 45 may illuminate indicator lights 61 in a certain pattern to denote that the retrieved access code has been rejected (i.e., deemed unacceptable).

Referring now to FIG. 5(*c*), with latch 51 disengaged from drawer 37, the user grasps flange 39-3 and rotates disposal drawer 37 forward from its closed position to its open position, as represented by arrow C. While holding drawer 37 open, the user then drops the safety container through slot 35 so that it rests on the interior surface of central tray 39. Having placed the safety container on tray 39, the disposal drawer 37 is released. The spring biased nature of disposal drawer 37 causes it rotate from its open position to its closed position (as represented by arrow D in FIG. 5(*d*)) in a smooth and gradual manner. As disposal drawer 37 pivots closed, the safety container slides along central tray 39 and eventually drops into collection bin 29 through open top end 30.

Immediately after disposal drawer 37 returns to its closed position, drawer sensor 67 sends an appropriate signal to controller 45. In response thereto, controller 45 de-energizes solenoid 53 which, in turn, projects piston 53-1 outward, as represented by arrow E in FIG. 5(*d*). It is to be understood that the outward projection of piston 53-1 displaces latch 51 back to its original locked position, as shown FIG. 5(*a*). As such, disposal drawer 37 is effectively locked in its closed position.

As safety containers collect within bin 29, sonar sensor 63 routinely measures the waste level (i.e., to prevent overflow, jamming, etc.) and sends the results of the waste level measurements to controller 45. Once sonar sensor 63 measures collection bin 29 as being three-quarters full, controller 45 in turn temporarily illuminates (i.e., flashes) yellow indicator light 61-2 every two seconds, thereby signifying that a bin pick-up is required. Once sonar sensor 63 measures collection bin 29 as being completely full, controller 45 in turn (i) temporarily illuminates (i.e., flashes) red indicator light 61-1 every two seconds and (ii) retains disposal drawer 37 locked in its closed position under all circumstances (i.e., even upon receiving a valid access code) in order prevent overfilling.

In order to replace collection bin 29, a waste disposal professional unlocks access panel 33, pivots panel 33 open and removes collection bin 29 from housing 13. An empty collection bin 29 is then disposed inside housing 13 and door 33 is locked shut. In this manner, only authorized waste management professionals are provided access to the medical refuse collecting within bin 29.

If a collection bin 29 is not placed within interior cavity 27, bin detection sensor 65 will send an appropriate signal to controller 45. In response thereto, controller 45 will illuminate red indicator light 61-1, yellow indicator light 61-2 and red indicator light 61-1 in rapid succession every two seconds to signify that a collection bin 29 is required. For safety purposes, controller 45 will retain disposal drawer 37 locked in its closed position until a collection bin 29 is placed within interior cavity 27.

If the voltage supplied to controller 45 from the power source falls beneath a predefined threshold, controller 45 will illuminate red indicator light 61-1 and yellow indicator light 61-2 in rapid succession every ten seconds to signify that the power source needs to be replaced.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A receptacle for medical refuse, the receptacle comprising:
   - (a) a housing comprising a front panel, a rear panel, a top panel, a bottom panel, a left side panel and a right side panel which together define an interior cavity that is sized and shaped to receive a bin for collecting medical refuse, the housing being shaped to define a slot formed in the top panel for depositing refuse into the bin and a separate opening formed in the front panel for withdrawing the bin from the interior cavity, both the slot and the opening being in communication with the interior cavity,
   - (b) a drawer coupled to the housing and pivotable between closed and open positions, the drawer fully enclosing the slot when disposed in its closed position, the drawer at most partially enclosing the slot when disposed in its open position,
   - (c) a latch disposable between first and second positions, the drawer being retained in its closed position by the latch when disposed in its first position, the drawer being capable of pivotable displacement between its closed and open positions when the latch is disposed in its second position,
   - (d) a electronic controller for regulating the position of the latch,
   - (e) a lockable access panel coupled to the housing and pivotable between closed and open positions, the access panel enclosing the opening for withdrawing refuse when disposed in its closed position,
   - (f) a sensor disposed within the interior cavity of the housing for measuring the level of medical refuse collected within the bin, the sensor being electrically connected to the electronic controller, wherein the electronic controller is programmed to retain the latch in its first position when the measured level of medical refuse collected within the bin exceeds a predefined threshold, and
   - (g) a display electrically connected to the controller, the display providing indication when the measured level of medical refuse collected within the bin exceeds the predetermined threshold.

2. The receptacle as claimed in claim 1 wherein the sensor measures the level of medical refuse collected within the bin using sonar.

3. The receptacle as claimed in claim 1 wherein the electronic controller is adapted to receive a first access code for authorizing access to the interior cavity through the slot for depositing refuse.

4. The receptacle as claimed in claim 3 wherein the electronic controller is programmed to cross-reference the first access code against a second access code stored in memory in the electronic controller.

5. The receptacle as claimed in claim 4 wherein the electronic controller is programmed to displace the latch from its first position to its second position upon verifying that the first access code matches the second access code.

6. The receptacle as claimed in claim 5 further comprising an automatic identification reader for automatically retrieving the first access code, the automatic identification reader being electrically connected to the electronic controller.

7. The receptacle as claimed in claim 6 wherein the automatic identification reader is in the form of a barcode scanner.

8. The receptacle as claimed in claim 1 wherein the display includes a plurality of individually operating light emitting diodes, each light emitting diode being electrically connected to the controller.

9. The receptacle as claimed in claim 1 further comprising a solenoid for regulating the position of the latch, the solenoid being electrically connected to the electronic controller.

10. The receptacle as claimed in claim 1 wherein the drawer is naturally biased to its closed position.

11. The receptacle as claimed in claim 1 wherein the disposal drawer is in the form of a roll bucket which includes a central tray and a pair of end pieces, the pair of end pieces being formed on opposite sides of the central tray.

12. The receptacle as claimed in claim 11 wherein the central tray for the disposal drawer includes a substantially planar section and an arcuate section which are formed together.

* * * * *